United States Patent
Kim et al.

(10) Patent No.: US 12,083,093 B2
(45) Date of Patent: Sep. 10, 2024

(54) COMPOSITION FOR PREVENTING OR TREATING CELLULAR SENESCENCE-RELATED DISEASES COMPRISING SALINOMYCIN AS EFFECTIVE COMPONENT

(71) Applicant: RESEARCH COOPERATION FOUNDATION OF YEUNGNAM UNIVERSITY, Gyeongsan-si (KR)

(72) Inventors: Jae-Ryong Kim, Daegu (KR); Eok-Cheon Kim, Wonju-si (KR); Kyong-Jin Jung, Daegu (KR); You Lim Son, Daegu (KR)

(73) Assignee: RESEARCH COOPERATION FOUNDATION OF YEUNGNAM UNIVERSITY, Gyeongsan-si (KR)

( * ) Notice: Subject to any disclaimer, the term of this patent is extended or adjusted under 35 U.S.C. 154(b) by 674 days.

(21) Appl. No.: 17/413,088

(22) PCT Filed: Oct. 11, 2019

(86) PCT No.: PCT/KR2019/013373
§ 371 (c)(1),
(2) Date: Jun. 11, 2021

(87) PCT Pub. No.: WO2020/122393
PCT Pub. Date: Jun. 18, 2020

(65) Prior Publication Data
US 2022/0008377 A1    Jan. 13, 2022

(30) Foreign Application Priority Data

Dec. 13, 2018    (KR) .................. 10-2018-0161044

(51) Int. Cl.
*A61K 31/35*    (2006.01)
*A61P 9/10*    (2006.01)
(Continued)

(52) U.S. Cl.
CPC ............ *A61K 31/35* (2013.01); *A61P 9/10* (2018.01); *A61P 11/00* (2018.01); *A61P 13/12* (2018.01); *A61P 19/04* (2018.01); *A61P 27/02* (2018.01)

(58) Field of Classification Search
CPC .. A61K 31/35; A61P 9/10; A61P 11/00; A61P 13/12; A61P 19/04; A61P 27/02; A61P 19/00; A61P 39/06
See application file for complete search history.

(56) References Cited

FOREIGN PATENT DOCUMENTS

KR    10-2016-0092550 A    8/2016

OTHER PUBLICATIONS

Mirkheshti, N. et al. Dual targeting of androgen receptor and mTORCI by salinomycin in prostate cancer. Oncotarget. Aug. 19, 2016, vol. 7, No. 38, pp. 62240-62254.*

(Continued)

*Primary Examiner* — Deborah D Carr
(74) *Attorney, Agent, or Firm* — NSIP Law

(57) ABSTRACT

The present invention relates to a composition for preventing or treating cellular senescence-associated diseases comprising salinomycin as an active ingredient, which acts differently depending on the type of senescent cells, and it was confirmed that salinomycin exhibits a senomorphics effect of restoring the function and morphology of fibroblasts and vascular endothelial cells in which senescence is induced and exhibits a senolytics effect of selectively killing aging-induced retinal pigmented epithelial cells, and exhibits a senomorphics effect of restoring the function and morphology of cells, and thus the salinomycin acts differently depending on the type of cells to effectively prevent or treat senile eye disease, tissue fibrosis disease, atherosclerosis, osteoarthritis, degenerative brain disease, chronic skin (Continued)

damage, obesity and diabetes caused by cellular aging and can be provided as a composition for life extension.

6 Claims, 20 Drawing Sheets

(51) Int. Cl.
*A61P 11/00* (2006.01)
*A61P 13/12* (2006.01)
*A61P 19/04* (2006.01)
*A61P 27/02* (2006.01)

(56) References Cited

OTHER PUBLICATIONS

Astle, M. V. et al. AKT induces senescence in human cells via mTORCI and p53 in the absence of DNA damage: implications for targeting mTOR during malignancy. Oncogene. 2012, vol. 31, pp. 1949-1962.*

Astle, Megan V., et al. "AKT induces senescence in human cells via mTORC1 and p53 in the absence of DNA damage: implications for targeting mTOR during malignancy." *Oncogene*, 31, 15, 2012 (pp. 1949-1962).

Al Dhaheri, Yusra, et al. "Salinomycin induces apoptosis and senescence in breast cancer: upregulation of p21, downregulation of survivin and histone H3 and H4 hyperacetylation." *Biochimica et Biophysica Acta* (*BBA*)-*General Subjects*, 1830, 4, 2013 (pp. 3121-3135).

Mirkheshti, Nooshin, et al. "Dual targeting of androgen receptor and mTORC1 by salinomycin in prostate cancer." *Oncotarget*, 7, 38, 2016 (pp. 62240-62254).

Milanovic, Maja, et al. "Senescence-associated reprogramming promotes cancer stemness." *Nature*, 553,7686, 2018 (pp. 96-100).

Myrianthopoulos, Vassilios. "The emerging field of senotherapeutic drugs." *Future Medical Chemistry*, 2018 (pp. 2369-2372).

International Search Report issued on Feb. 7, 2020 in counterpart International Patent Application No. PCT/KR2019/013373 (3 pages in English and 3 pages in Korean).

* cited by examiner

HK-2

COMPOSITION FOR PREVENTING OR TREATING CELLULAR SENESCENCE-RELATED DISEASES COMPRISING SALINOMYCIN AS EFFECTIVE COMPONENT

CROSS REFERENCE TO RELATED APPLICATIONS

This application is a U.S. National Stage Application of International Application No. PCT/KR2019/013373, filed on Oct. 11, 2019, which claims the benefit under 35 USC 119(a) and 365(b) of Korean Patent Application No. 10-2018-0161044, filed on Dec. 13, 2018, in the Korean Intellectual Property Office, the entire disclosure of which is incorporated herein by reference for all purposes.

TECHNICAL FIELD

The present invention relates to a composition for preventing or treating cellular senescence-associated diseases comprising as an active ingredient salinomycin, which acts differently depending on the type of senescent cells.

BACKGROUND ART

Senescent cells accumulate in individual tissues and organs with aging, and accumulation of senescent cells not only induces changes in the function and structure of tissues and organs due to aging, but also plays an important role in the etiology of various senescence-associated diseases such as cancer, diabetes, obesity, tissue fibrosis, senile eye diseases, cardio-cerebrovascular disease, degenerative brain disease, osteoarthritis, skin aging and chronic skin wounds, etc. Therefore, it has been suggested that delaying or overcoming aging is the most effective method for the prevention and treatment of senescence-associated diseases such as cancer, diabetes, and cardiovascular disease.

Rapamycin, SIRT1 activator, calorie-limiting mimetic, AMPK activator, and telomerase activator are promising as aging control drugs. In addition, recently, senotherapeutics, which target senescent cells, have been developed and their efficacy has been reported at the cellular level and in animal models. Senotherapeutics are divided into senolytics, which selectively kill only senescent cells, and senomorphics, which restore the function or shape of senescent cells like young cells.

Quercetin and dasatinib, which are Bcr-Abl protein kinase inhibitors, ABT263 and ABT737, which are Bcl-2 kinase inhibitors, and A1331852 and A1155463, which are BCL-XL inhibitors, and UBX0101, which is an MDM2/p53 inhibitor, FOXO4-DRI, which is p53 inhibitor, and 17-DMAG, which is HSP90 inhibitor, have been recently reported as senolytics. As senomorphics, mTOR inhibitors such as rapamycin, IKK/NFkB inhibitors, free radical scavengers and JAK inhibitors have been reported.

Accordingly, research and development for preventing or treating senescence-associated diseases are actively progressing through the development of senotherapeutics that target senescence and senescent cells.

Salinomycin is a monocarboxylic polyether antibiotic isolated from *Streptomyces albus*, and is used as a therapeutic agent for coccidiosis, a parasitic disease in chickens, but no specific efficacy against senescent cells has been reported yet.

DISCLOSURE

Technical Problem

The present invention provides a composition comprising salinomycin as an active ingredient to selectively kill senescent cells or restore the function and morphology of senescent cells to provide a composition for improving or treating diseases caused by cellular aging.

Technical Solution

The present invention provides a senomorphics composition comprising salinomycin as an active ingredient.

The present invention provides a senolytics composition comprising salinomycin as an active ingredient.

The present invention provides a pharmaceutical composition for preventing or treating cellular senescence-associated diseases comprising salinomycin as an active ingredient.

In addition, the present invention provides a composition for improving aging or extending life comprising salinomycin as an active ingredient.

Advantageous Effects

According to the present invention, it was confirmed that salinomycin exhibits a senomorphics effect of restoring the function and morphology of aging-induced fibroblasts and vascular endothelial cells, while senolytics effect of selectively kills aging-induced retinal pigmented epithelial cells, and thus the salinomycin acts differently depending on the type of cells to effectively prevent or treat obesity, diabetes, degenerative neurological disease, bone bronchiolitis, atherosclerosis, chronic skin damage, senile eye disease and tissue fibrosis disease caused by cellular aging and can be provided as a composition for whitening skin and life extension.

DESCRIPTION OF DRAWINGS

FIG. 1A shows a result of treatment with 100 nM rapamycin, 100 nM ABT263 and 100 nM salinomycin on young fibroblasts (HDF) and premature senescent fibroblasts by doxorubicin, and SAβG activity staining after 4 days; FIG. 1B shows a result of the SAβG activity level; and FIG. 1C shows a result of confirming the degree of cell survival. HDF=human dermal fibroblasts, Young=young cells, Dox=doxorubicin, NT=0.01% DMSO, Rap=100 nM rapamycin, ABT=100 nM ABT263, Sal=100 nM salinomycin (**, $p<0.01$).

FIG. 2A shows a result of treatment with 100 nM ABT263 and 100 nM salinomycin on young fibroblast (HDF) and replicative senescent fibroblasts, and SAβG activity staining after 4 days; FIG. 2B shows a result showing the staining level; FIG. 2C shows a Western blot analysis result confirming the expression levels of p53 and p16, which are cell aging-related proteins; and FIG. 2D shows a result of confirming the cell survival according to the concentration of salinomycin. HDF=human dermal fibroblasts, Young=young cells, Senescent=replicative senescent cells, NT=0.01% DMSO, ABT=100 nM ABT263, Sal=100 nM salinomycin (*, $p<0.05$; **, $p<0.01$).

FIG. 3A shows a result of treatment with a 100 nM rapamycin, 100 nM ABT263 and 100 nM salinomycin on young vascular endothelial cells (HUVEC) and premature senescent vascular endothelial cells by doxorubicin, and confirming SAβG activity staining after 4 days; FIG. 3B shows a result of the level of SAβG activity staining; and FIG. 3C shows a result of confirming cell survival. HUVEC=human umbilical vascular endothelial cells, Young=young cells, Dox=doxorubicin, NT=0.01% DMSO, Rap=100 nM rapamycin, ABT263=100 nM ABT263, Sal=100 nM salinomycin (**, p<0.01).

FIG. 4A shows a result of treatment with 100 nM rapamycin and 100 nM salinomycin on young vascular endothelial cells (HUVEC) and replicative senescent vascular endothelial cells, and confirming SAβG activity staining after 4 days; FIG. 4B shows a result of the SAβG activity staining level; FIG. 4C shows a result of confirming the cell survival according to the concentration of salinomycin. HUVEC=human umbilical vascular endothelial cells, Young=young cells, Senescent=replication senescent cells, NT=0.01% DMSO, Rap=100 nM rapamycin, ABT=100 nM ABT263, Sal=100 nM salinomycin (*, p<0.05; **, p<0.01).

FIG. 5A shows a result of staining picture of treatment with 100 nM rapamycin, ABT263 and 100 nM salinomycin on young retinal pigmented epithelial cells (ARPE) and premature senescent retinal pigmented epithelial cells by doxorubicin, and confirming SAβG activity staining after 4 days; FIG. 5B shows a result of confirming the cell survival; and FIG. 5C shows a result of confirming the cytotoxic effect by performing LDH activity analysis. ARPE=adult retinal pigmented epithelial cells, Young=young cells, Dox=doxorubicin, NT=0.01% DMSO, ABT=100 nM ABT263, Sal=100 nM salinomycin (**, p<0.01).

FIG. 6A shows a cell photograph of treatment with 100 nM ABT263, 100 nM rapamycin, 100 nM salinomycin on premature senescent human renal tubular cells (HK2) by doxorubicin, and after 4 days; FIG. 6B shows a result of confirming cell survival; and FIG. 6C shows a result of performing SAβG activity staining. HK2=human tubular epithelial cells, Dox=doxorubicin, NT=0.01% DMSO, Rap=100 nM rapamycin, ABT=100 nM ABT263, Sal=100 nM salinomycin.

FIG. 7A is a schematic diagram showing the experimental process; FIG. 7B shows a result of confirming the weight change before the experiment and after kidney resection; FIG. 7C shows a result of plasma creatinine concentration; FIG. 7D shows a result of the plasma BUN concentration; FIG. 7E shows a result of hematoxylin-eosin staining, trichrome staining and PAS staining of the tissue sample; FIG. 7F shows a result of the degree of fibrosis of the tissue after trichrome staining in the sample; FIG. 7G shows a result of confirming the degree of cellular senescence in the tissue by Sudan Black B staining; FIG. 7H shows a result of confirming the lipid peroxide level in the tissue; FIG. 7I shows a result of performing MDA analysis in the tissue; FIG. 7J shows a result of confirming the level of superoxides in the tissue; FIG. 7K shows a result of confirming the expression level of 4-HNE and p16 protein in the tissue by Western blot analysis; FIG. 7L shows a result of Western blot analysis of tissue proteins, and FIG. 7M shows a result of densitometry analysis of western blot result. Sham=no ischemia-reperfusion injury, PBS=ischemia-reperfusion injury, HHT=ischemia-reperfusion injury followed by salinomycin intraperitoneal injection, UIRI=left kidney ischemia-reperfusion injury, UNx=right kidney resection, PAS=periodic acid-Schiff, MDA=malondialdehyde, 4-HNE=4-hydroxynonenal, pRb=phosphorylated Rb, COL1=collagen type I, α-SMA=alpha-smooth muscle actin, SOD2=superoxide dismutase 2 (**, p<0.01, *, p<0.05).

FIG. 8A is a schematic diagram summarizing the experimental process; and FIG. 8B shows a result of confirming the change in body weight in the experimental process; FIG. 8C shows a result of performing hematoxylin-eosin (H&E) and trichrome staining of lung tissue samples; and FIG. 8D shows a result of confirming the level of lung fibrosis in the tissue sample. D=salinomycin or PBS intraperitoneal injection, NT=not treated, PBS=PBS intraperitoneal injection, Sal=salinomycin intraperitoneal injection (**, p<0.01).

FIG. 9A is a schematic diagram showing an experimental process; FIG. 9B shows a result of confirming a change in body weight in the experimental process; FIG. 9C shows a result of performing Hematoxylin-eosin and trichrome staining in an abdominal wall tissue sample; and FIG. 9D shows a result of confirming the thickness of peritoneal mesothelial cell layer in a tissue sample. CHG=chlorhexidine gluconate, D=salinomycin or DMSO intraperitoneal injection, NT=not treated, DMSO=DMSO intraperitoneal injection, Sal=salinomycin intraperitoneal injection (**, p<0.01).

BEST MODE

Figure 1A:
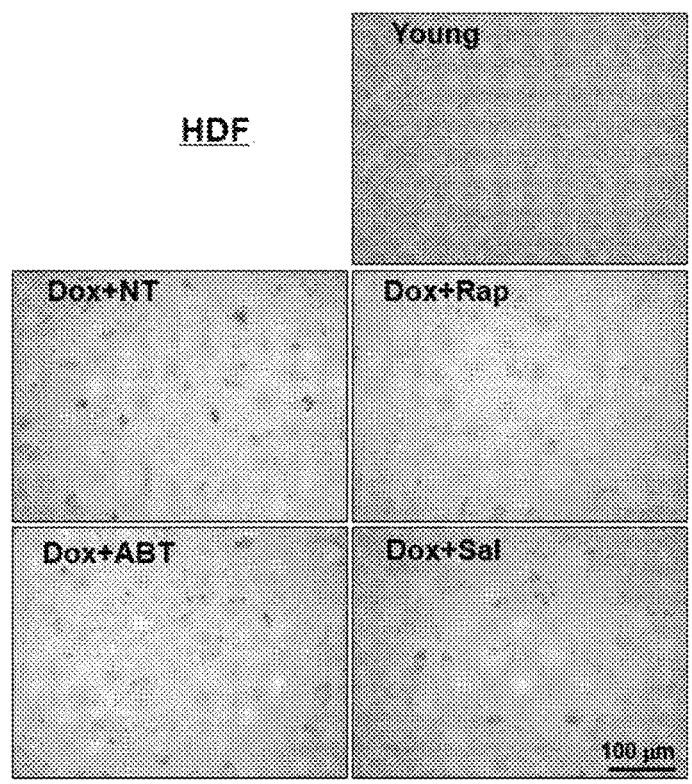
FIGS. 1A-1C show results of confirming the senomorphics action of salinomycin in premature senescent human fibroblasts induced by doxorubicin.

Hereinafter, the present invention will be described in more detail.

As it is reported that when aging cells present in tissues are removed from animal models, the morphology and function of tissues and organs due to aging are improved to treat senescence-associated diseases, the health life is increased, the inventors of the present invention conducted research on senotherapeutics targeting senescent cells to confirm that salinomycin acts differently depending on the type of senescent cells, thereby improving diseases caused by cellular aging and prolonging the lifespan of cells and completed the present invention.

The present invention can provide a senomorphics composition comprising salinomycin as an active ingredient.

More specifically, the senomorphics may restore the function of the senescent cells to normal cells.

The senescent cells may be selected from the group consisting of fibroblasts and vascular endothelial cells in which senescence is induced by drug treatment or subculture.

The present invention may comprise salinomycin as an active ingredient, and the salinomycin can provide a reagent composition for senomorphics which restores the function or morphology of senescent cells to normal cells in vitro.

In addition, the present invention can provide a method of killing senescent cells comprising treating salinomycin on fibroblasts or renal tubular epithelial cells isolated from mammals other than humans in vitro.

The present invention may provide a senolytics composition comprising salinomycin as an active ingredient.

The senolytics may selectively kill senescent cells.

The senescent cells may be the senescent cells are retinal pigmented epithelial cells in which senescence is induced by drug treatment or subculture.

The present invention may comprise salinomycin as an active ingredient, and the salinomycin can provide a reagent composition for senolytics which kills senescent cells in vitro.

The present invention may comprise salinomycin as an active ingredient, and the salinomycin can provide a reagent composition for senolytics which kills aged cells in vitro.

In addition, the present invention can provide a method of killing senescent cells comprising treating salinomycin on retinal pigmented epithelial cells isolated from mammals other than humans in vitro.

The present invention can provide a pharmaceutical composition for preventing or treating cellular senescence-associated diseases comprising salinomycin as an active ingredient.

The salinomycin may prevent or treat diseases induced by cellular aging by selectively killing senescent cells or restoring a function or morphology of the senescent cells to normal cells.

The cellular senescence-associated disease may be selected from the group consisting of tissue fibrosis, senile eye disease, atherosclerosis, osteoarthritis, degenerative brain disease, obesity, diabetes and chronic skin damage.

In more detail, the tissue fibrosis may be selected from the group consisting of renal fibrosis, pulmonary fibrosis and peritoneal fibrosis, but it is not limited thereto.

The senile eye disease may be selected from the group consisting of cataract, glaucoma, and macular degeneration, but it is not limited thereto.

The degenerative brain disease may be selected from the group consisting of Parkinson's disease, Alzheimer's disease and stroke, but it is not limited thereto.

In one embodiment of the present invention, the pharmaceutical composition comprising salinomycin as an active ingredient may be used as any one formulation selected from the group consisting injections, granules, powders, tablets, pills, capsules, suppositories, gels, suspensions, emulsions, drops or solutions according to the conventional method.

In another embodiment of the present invention, the pharmaceutical composition comprising salinomycin as an active ingredient may further comprise at least one additive selected from the group consisting of carriers, excipients, disintegrants, sweeteners, coating agents, swelling agents, lubricants, slip modifiers, flavors, antioxidants, buffers, bacteristats, diluents, dispersants, surfactants, binders and lubricants, which are conventionally used for the preparation of the pharmaceutical composition.

Specifically, examples of the carrier, excipient and diluent include lactose, dextrose, sucrose, sorbitol, mannitol, xylitol, erythritol, maltitol, starch, acacia rubber, alginate, gelatin, calcium phosphate, calcium silicate, cellulose, methylcellulose, microcrystalline cellulose, polyvinylpyrrolidone, water, methylhydroxybenzoate, propylhydroxybenzoate, talc, magnesium stearate and mineral oil. Solid formulations for oral administration include tablets, pills, powders, granules, capsules, etc., and such solid formulations may contain at least one excipient such as starch, calcium carbonate, sucrose or lactose, gelatin and the like in addition to the composition. Furthermore, in addition to simple excipients, lubricants such as magnesium stearate and talc are also used. Examples of the liquid formulations for oral administration include suspensions, solutions, emulsions, syrups and the like, and various excipients such as wetting agents, sweeteners, fragrances, preservatives and the like may be included in addition to water and liquid paraffin which are commonly used as simple diluents. Formulations for parenteral administration include sterile aqueous solutions, non-aqueous solutions, suspensions, emulsions, freeze-dried preparations, suppositories and the like. Examples of the non-aqueous solution and the suspension include propylene glycol, polyethylene glycol, vegetable oil such as olive oil, injectable ester such as ethyl oleate, and the like. As the base of the suppository, witepsol, macrogol, tween 61, cacao butter, laurinum, glycerogelatin and the like can be used.

According to one embodiment of the invention, the pharmaceutical composition may be administered intravenously, intraarterially, intraperitoneally, intramuscularly, intrasternally, transdermally, nasally, inhaled, topically, rectally, orally, intraocularlly or intradermally to the subject in the conventional manner.

The preferred dosage of salinomycin may vary depending on the condition and weight of the subject, the type and extent of the disease, the drug form, the route of administration, and the duration, and may be appropriately selected by those skilled in the art. According to one embodiment of the present invention, the daily dosage may be, but is not limited to, 0.01 to 200 mg/kg, specifically 0.1 to 200 mg/kg, more specifically 0.1 to 100 mg/kg. Administration may be administered once a day or divided into several times, and the scope of the invention is not limited thereto.

In the present invention, the 'subject' may be a mammal including a human, but it is not limited thereto.

In addition, the present invention can provide a composition for improving aging or extending life, comprising salinomycin as an active ingredient.

Hereinafter, the present invention will be described in more detail through examples. These examples are only intended to illustrate the present invention in more detail, and it will be apparent to those skilled in the art that the scope of the present invention is not limited by these examples according to the gist of the present invention. The examples of the present invention are provided to more completely explain the present invention to those of ordinary skill in the art.

The following experimental examples are intended to provide experimental examples commonly applied to each of the examples according to the present invention.

<Experimental Example 1> Cell Culture

Human dermal fibroblast (HDF) and human umbilical vascular endothelial cells (HUVEC) were purchased from LONZA Inc. In (Walkersville, MD), and human retinal pigmented epithelial cells (ARPE-19) and HK2 cells (human tubular epithelial cells) were purchased from ATCC (Manassas, VA), respectively and used.

Human fibroblasts were cultured in DMEM (Dulbecco's Modified Eagle Medium) culture solution containing 10% fetal bovine serum (FBS), human umbilical vascular endothelial cells were cultured in EGM-2 culture solution, human retinal pigmented epithelial cells were cultured in DMEM:F12 culture solution containing 10% FBS, and HK-2 cells were cultured in RPMI1640 culture solution containing 10% FBS.

Cells ($2 \times 10^5$) were dispensed into a 100 mm culture dish and subcultured in a 37° C., 5% $CO_2$ incubator. When the cells grew to 80-90% in the culture dish, the cells were separated from the culture dish by treatment with a trypsin-EDTA solution, and the number of cells was measured.

The degree of cell growth was confirmed by the cell population doubling time (PDT) as shown in the following equation.

$$PDT=((T-T_0)\log 2)/(\log N-\log N_0)$$

(N=number of cells grown in the culture dish, $N_0$=number of first dispensed cells, $T-T_0$=cell culture time)

<Experimental Example 2> Preparation of Premature Senescent Cells by Treatment with Doxorubicin Each cell was treated in a serum-free culture solution containing doxorubicin (0.5 μM) for 4 hours. After washing the cells with a serum-free culture solution, the cells were cultured for 4 days in a culture solution containing 10% FBS, and then cellular aging was confirmed by measuring the level of senescence by staining with senescence-associated beta galactosidase.

<Experimental Example 3> Preparation of Replicative Senescent Cells

After dispensing $2 \times 10^5$ cells in a 100 mm culture dish, they were cultured in a 37° C., 5% $CO_2$ incubator. When the cells grew to 80-90% in the culture dish, the cells were removed by treatment with trypsin-EDTA, and the number of cells was measured, and the cell population doubling time (PDT) was measured.

By successively subculturing the cells in the same process as described above, replication aging was induced. PDT of young fibroblasts was 36 hours, PDT of replicative senescent fibroblasts was 12 days, PDT of young vascular endothelial cells was 24 hours, and PDT of replicative senescent vascular endothelial cells was 7 days.

The level of cellular senescence was confirmed by staining of senescence-associated beta galactosidase and analysis of p53 and p16 protein expressions.

<Experimental Example 4> Confirmation of Effective Substances of Senolytics and Senomorphics from Clinical Test Compounds 2,150 clinical trial compounds were distributed from Korea Chemical Bank.

Human fibroblasts and human vascular endothelial cells, in which premature senescence was induced by treatment with doxorubicin were dispensed into a 96-well plate, and then 2,150 compounds were treated at a concentration of 100 nM for 4 days, respectively. The degree of survival of senescent cells was investigated by CCK-8 analysis, and the degree of senescence of cells was investigated by senescence-associated beta galactosidase staining.

<Experimental Example 5> Drug Treatment

Salinomycin was purchased from TOCRIS Bioscience (Minneapolis, MN, USA), rapamycin was purchased from EMD Millipore (Burlington, MA, USA), and ABT263 was purchased from Selleckchem (Houston, TX, USA).

After each sample was dissolved in DMSO, young cells, replicative senescent cells and senescent cells in which premature aging was induced by treating with doxorubicin were treated with 100 nM salinomycin, 100 nM rapamycin, 100 nM ABT263. After incubation for 4 days in a 37° C., 5% $CO_2$ incubator, the degree of cell survival was confirmed by CCK-8 analysis, the degree of cellular aging was confirmed by senescence-associated β-galactosidase (SAβG) staining, p53 and p16 protein expression analysis.

<Experimental Example 6> Analysis of Senescence-Associated β-Galactosidase (SAβG) Staining The cells were washed with 1× phosphate buffer solution, and fixed with a phosphate buffer solution containing 3.7% (v/v) paraformaldehyde. After adding 1 mg/ml 5-bromo-4-chloro-3-indolyl-β-D-galactoside, 40 mM citric acid-sodium phosphate (pH 6.0), 5 mM potassium ferricyanide, 5 mM potassium ferrocyanide, 150 mM NaCl, and 2 mM $MgCl_2$ solution, it was reacted at 37° C. for 18 hours. It was stained with eosin as a control stain and cells stained blue in the cytoplasm were identified using an optical microscope.

<Experimental Example 7> Cell Survival Analysis (Cell Counting Kit-8 Assay; CCK-8)

Young cells ($1 \times 10^3$ cells/well) or senescent cells ($2 \times 10^3$ cells/well) were dispensed into a 96-well plate, and cultured overnight in a 37° C., 5% $CO_2$ incubator. Salinomycin, ABT263 and rapamycin were treated at each concentration, and then incubated for 4 days in a 37° C., 5% $CO_2$ incubator. 10 μl of CCK-8 reagent (Dojindo Molecular Technologies Inc., Kumamoto, Japan) was added to each well, and incubated for 2 hours in an incubator. Then, the absorbance was measured at 450 nm using a Microplate reader.

The degree of cell survival was expressed as a relative value for the absorbance of the control group treated with only DMSO as 100%.

<Experimental Example 8> Lactate Dehydrogenase Assay (LDH)

Cytotoxicity against young and senescent cells was investigated with a lactate dehydrogenase (LDH) activity kit (Dojindo Molecular Technologies Inc.). Young cells ($1 \times 10^3$ cells/100 μl/well) or senescent cells ($2 \times 10^3$ cells/100 μl/well) were dispensed into a 96-well plate, and then cultured overnight in a 37° C., 5% $CO_2$ incubator.

Salinomycin, ABT263 and rapamycin were treated at each concentration, and then incubated for 4 days in a 37° C., 5% $CO_2$ incubator. After transferring the cell culture solution to a 1.5 ml tube, it was centrifuged at 4° C. and 12,000 rpm. 100 μl of the supernatant was dispensed into a 96-well plate, and 100 μl of the LDH measurement solution was added to each well, followed by reaction in a $CO_2$ incubator for 30 minutes. 50 μl of the LDH reaction stop solution was added, and absorbance was measured at 490 nm using a microplate reader. The level of LDH activity was expressed as a relative value based on the absorbance of the control group treated with only DMSO.

<Experimental Example 9> Preparation of Ischemia-Reperfusion Injury Induced Experimental Animal Animal experiments were performed with the approval of the Animal Experimental Ethics Committee, Yeungnam University College of Medicine (YUMC-AEC2018-024). C57BL/6J 8-week-old male mice were anesthetized by intraperitoneal injection of 2.5% Avertin (0.025 ml/g body weight). The mouse was placed on a hot plate at 37° C., and the left flank was incised to expose the left kidney. The renal arteriovenous blood vessels were ligated with a microaneurism clamp (Roboz), and whether the blood vessels were blocked or not was confirmed by the color of the kidneys. During the induction of ischemia, the body temperature of the mice was maintained at 36.5-37.5° C. After 35 minutes, the clamp was removed and it was confirmed that reperfusion occurred.

As a control, renal arteriovenous vessels were not ligated, and the rest was performed in the same manner as above. From 4 days after ischemia-reperfusion injury, 2.5 µl of 10 mM salinomycin was diluted in 100 µl of phosphate buffer solution at intervals of 2 days and injected into the abdominal cavity 3 times (Sal group). The control group was a group that did not induce ischemia-reperfusion injury (Sham group) and an ischemia-reperfusion injury group (PBS) was used. Three mice were used for each group.

Figure 8A:
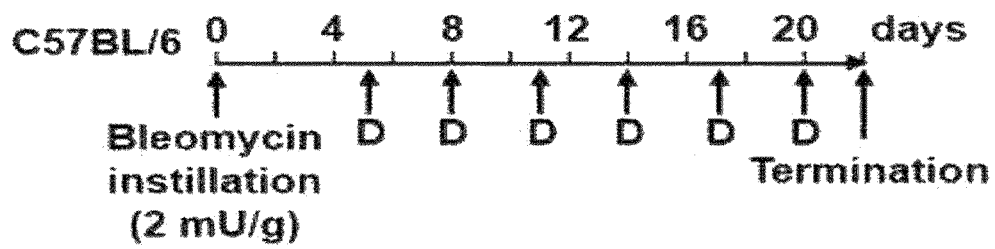
FIGS. 8A-8D show results of confirming the efficacy of salinomycin in an experimental animal in which pulmonary fibrosis was induced by bleomycin.

As shown in FIG. 8A, the right kidney was removed on the 10th day of the ischemia-reperfusion injury and sacrificed on the 11th day. The left kidney in which ischemia-reperfusion injury was induced, was excised in half and fixed in 10% formalin solution or stored frozen in liquid nitrogen.

<Experimental Example 10> Evaluation of Kidney Function

In order to evaluate kidney function due to ischemia-reperfusion injury, creatinine and blood urea nitrogen (BUN) concentrations in plasma and urine were measured.

Blood was collected from the retro-orbital vascular plexus of the mouse using a heparin capillary tube, and plasma was separated. Plasma creatinine was measured by QuantiChrom™ creatinine assay kit (DICT-500; BioAssay Systems, Hayward, CA, USA), and BUN was investigated by measuring absorbance at 490 nm and 450 nm by a spectrophotometer, respectively by BUN colorimetric detection kit (Arbor Assays, Ann Arbor, Michigan, USA).

<Experimental Example 11> Confirmation of Malondialdehyde (MDA), Lipid Peroxides (Hydroperoxides) and Superoxides ($O_2^-$)

To confirm the degree of lipid peroxidation in tissues, malondialdehyde (MDA) was confirmed by the TBARS method (Garcia Y J, et al., Journal of neuroscience methods. 2005).

Briefly, 1.4 ml of TBARS solution [0.375% thiobarbituric acid (TBA), 15% trichloroacetic acid (TCA), 0.25 N HCl] was added to the tissue pulverization solution (0.3 mg protein/0.1 ml), and boiled for 15 minutes at 95-100° C. and centrifugation was performed at 4° C. and 12,000 rpm for 10 minutes, and the absorbance of the supernatant was confirmed at 540 nm.

Lipid hydroperoxides were identified by ferrous ion oxidation xylenol orange (FOX) method (Jiang Z Y, et al., Lipids. 1991).

0.9 ml of FOX reagent (100 µM xylenol orange, 25 mM $H_2SO_4$, 0.1 M sorbitol, 2.5 mM ferrous ammonium sulfate] was reacted at room temperature for 30 minutes and then centrifuged to measure the absorbance of the supernatant at 570 nm.

Tissue superoxide was measured using dihydroethidium (DHE; Sigma, St. Louis, MO) (Peshavariya H M, et al., Free radical research. 2007). 0.2 ml of 10 µM DHE was added to 0.2 ml of the tissue pulverization solution and reacted at room temperature for 10 minutes. Fluorescence was measured at 37° C. with an Emax Precision Microplate Reader (Molecular Devices Corporation, Menlo Park, CA, USA) at 544 nm for excitation and 612 nm for emission.

<Experimental Example 12> Protein Extraction and Western Blot Analysis

After dispensing the cells into a 60 mm culture dish, the cells were cultured overnight in an incubator at 37° C. and 5% $CO_2$. After treatment with salinomycin, ABT263 and rapamycin, it was incubated for 3 days in a 37° C., 5% $CO_2$ incubator. After washing the cells with 1× phosphate buffer, RIPA buffer (12 mM EDTA, 137 mM NaCl, 20 mM Tris-HCl (pH 8.0), 1 mM $Na_3VO_4$ (Sigma-Aldrich, USA) 10 mM NaF (Sigma), 1 mM PMSF (Sigma), 1% Triton X-100, 10% glycerol, protease inhibition cocktail (Roche, Germany)) was added and lysed.

The lysed cells were transferred to a 1.5 ml tube, pipetted 3-4 times, and then left on ice for 20 minutes. After centrifugation at 12,000 rpm for 20 minutes to recover the supernatant, the protein concentration of the supernatant was quantified by BCA analysis.

RIPA buffer was added to the tissue and pulverized with WiseTis homogenizer HG-15D (DAIHAN Scientific, Seoul, South Korea). Centrifugation was performed at 12,000 rpm at 4° C. for 20 minutes, and the supernatant was transferred to a new tube. The protein concentration of the supernatant was quantified by the BCA method.

After electrophoresis (SDS-PAGE) of 30 µg of protein, Western blot analysis was performed. After electrophoresis, the protein was transferred from the gel to a polyvinylidene fluoride membrane (Pall Corporation). The membrane was treated with a 5% Difco™ skim milk solution (Becton, Dickinson and Company, USA) for 2 hours at room temperature, and the primary antibody was added, followed by reaction at room temperature for 2 hours.

As the primary antibody, anti-p53 antibody, anti-p16 antibody, anti-actin antibody and anti-GAPDH antibody were purchased from Santa Cruz Biotechnology, Inc. Anti-phosphorylated-Rb antibody was obtained from New England Biolabs (Ipswich, MA, USA), and the anti-SOD2 antibody and anti-catalase antibody were obtained from Bioworld Technology Inc. (Louis Park, MN, USA), anti-HNE antibody, anti-α-smooth muscle actin antibody, and anti-type I collagen antibody were purchased from Abcam (Cambridge, UK).

The membrane treated with the primary antibody was washed three times for 15 minutes each with TBST (20 mM Tris-HCl (pH 8.0), 137 mM NaCl, 0.1% Tween 20), and reacted for 60 minutes by treatment with the secondary antibody.

After washing for at least 60 minutes with TBST, protein expression was confirmed using an ECL detection kit (Elpis Biotech, Daejeon, South Korea).

<Experimental Example 13> Preparation of Experimental Animals for Lung Fibrosis

Animal experiments were conducted with the approval of the Animal Experimental Ethics Committee, Yeungnam University College of Medicine (YUMC-AEC2018-025). After anesthetizing by injecting 2.5% avertin (Avertin; 0.025 ml/g) into the abdominal cavity of 10-week-old C57BL/6J male mice, 2 mU/g of bleomycin was instilled into the bronchi and injected into the lungs. After bleomycin instillation, the weight was measured on the 3rd, 5th and 7th days, and mice that did not lose weight were excluded from the experiment.

From 5 days after bleomycin administration, 2.5 µl of 10 mM salinomycin was diluted in 100 µl phosphate buffer solution at intervals of 3 days and injected intraperitoneally 6 times (Sal group). On the other hand, the group that did not induce pulmonary fibrosis (NT group) and the group that injected only 2.5 µl DMSO-containing phosphate buffer (PBS) after bleomycin administration (PBS group) were used as a control group.

Three mice were used for each group, and lungs were excised by sacrifice 22 days after bleomycin injection and fixed in 10% formalin solution or stored frozen in liquid nitrogen.

<Experimental Example 14> Preparation of Experimental Animal for Peritoneal Fibrosis Animal experiments were conducted with the approval of the Animal Experimental Ethics Committee of Yeungnam University College of Medicine (YUMC-AEC2018-033). Peritoneal fibrosis mice experiments were performed using a model of peritoneal fibrosis induced by chlorhexidine gluconate (CHG) (Yoshio Y et al., Kidney international. 2004).

Figure 9A:
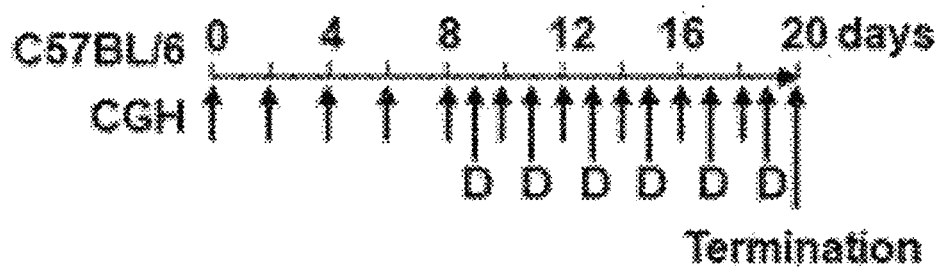
FIGS. 9A-9D show results of confirming the efficacy of salinomycin on peritoneal fibrosis caused by CHG in mice.
Figure 9B:
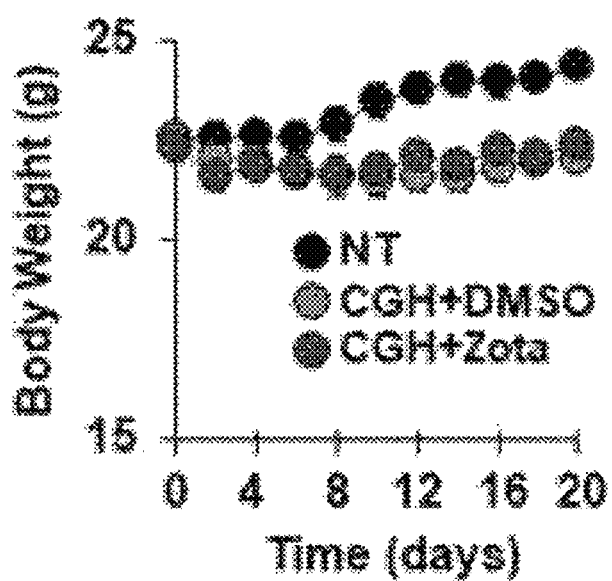

As shown in FIG. 9A, C57BL/6J 8-week-old male mice were intraperitoneally injected with a 0.1% CHG solution (0.1% CHG in a 15% ethanol phosphate buffer solution) at 10 ml/kg for 20 days at intervals of 2 days. From the 9th day, 2.5 µl of 10 mM salinomycin (Sal group) or 2.5 µl of DMSO (DMSO group) was diluted in 100 µl phosphate buffer solution and intraperitoneally injected at intervals of 2 days.

As a negative control (NT group), 100 µl of a 15% ethanol phosphate buffer solution was injected intraperitoneally instead of a 0.1% CHG solution. On the 20th day, the mice were sacrificed, the peritoneal tissue was excised, and the tissue was fixed in 4% paraformaldehyde solution.

<Experimental Example 15> Preparation and Staining of Tissue Samples

The tissue fixed in 10% formalin solution was embedded with paraffin and cut into 4 µm to prepare a tissue sample. After removing paraffin from the tissue sample, hematoxylin-eosin staining, trichrome staining, and PAS staining were performed.

The degree of fibrosis was measured by analyzing the degree of collagen staining using the i-Solution™ software program (IMT Inc., Canada) after trichrome staining and the degree of cell senescence in tissue samples was investigated by staining lipofuscin with Sudan black B (Viegas M S, et al., European journal of histochemistry: EJH. 2007). The degree of peritoneal fibrosis was confirmed by measuring the submesothelial thickness of the peritoneal mesothelial cell layer using the NIH Image J program.

<Example 1> Confirmation of Senomorphics Action of Salinomycin

1. Confirmation of Senomorphics Action of Salinomycin on Human Fibroblasts

Human fibroblasts were treated with doxorubicin and cultured for 4 days to induce early cellular senescence. Cells in which early senescence was induced were treated with 0.01% DMSO (NT), 100 nM salinomycin (Sal), 100 nM rapamycin (Rap) and 100 nM ABT263 (ABT), and 4 days later, SAβG activity staining was performed to confirm the degree of senescence of the cells, and the degree of cell survival was confirmed by performing CCK-8 analysis.

Rapamycin is a type of senomorphics known to inhibit cellular aging, and ABT263 is a type of senolytics known to induce senescent cell-specific apoptosis, and the above two drugs were used as positive controls.

Figure 1B:
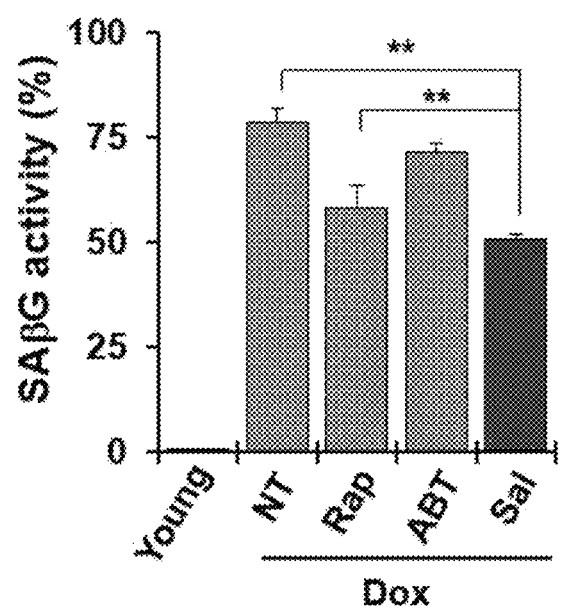
Figure 1C:
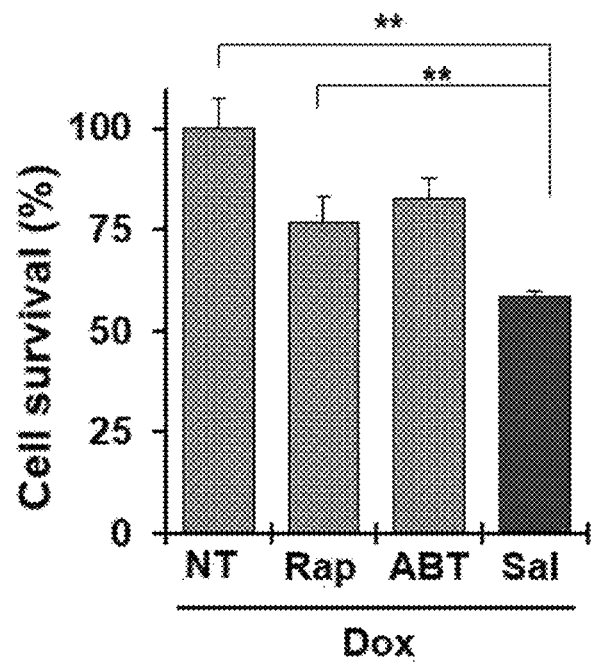

As a result of treatment of 100 nM salinomycin in human fibroblasts in which early cellular aging was induced by doxorubicin treatment, SAβG activity was significantly reduced compared to the DMSO-treated group as shown in FIG. 1A and FIG. 1B, and as shown in FIG. 1C, cell survival also decreased significantly ($p<0.01$). In addition, it was confirmed to be significantly reduced compared to those of rapamycin- and ABT263-treated experimental group.

In addition, it was confirmed whether salinomycin can reduce senescent cell-specific SAβG activity and cell growth in premature senescent human fibroblasts as well as replicative senescent human fibroblasts.

Figure 2A:
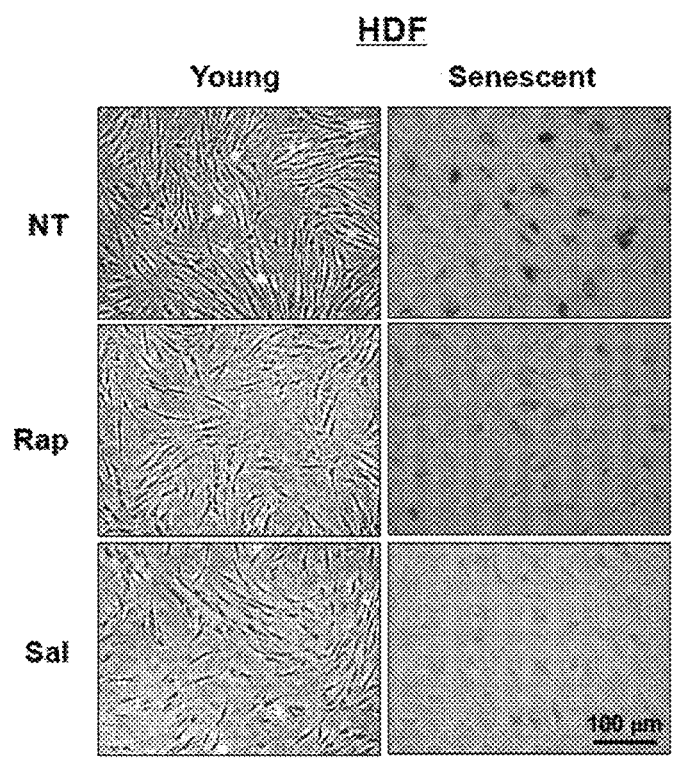
FIGS. 2A-2D show results of confirming the senomorphics action of salinomycin in replicative senescent human fibroblasts.
Figure 2B:
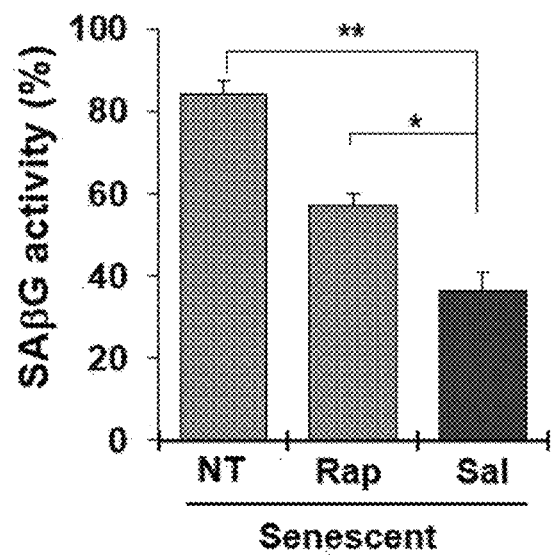
Figure 2C:
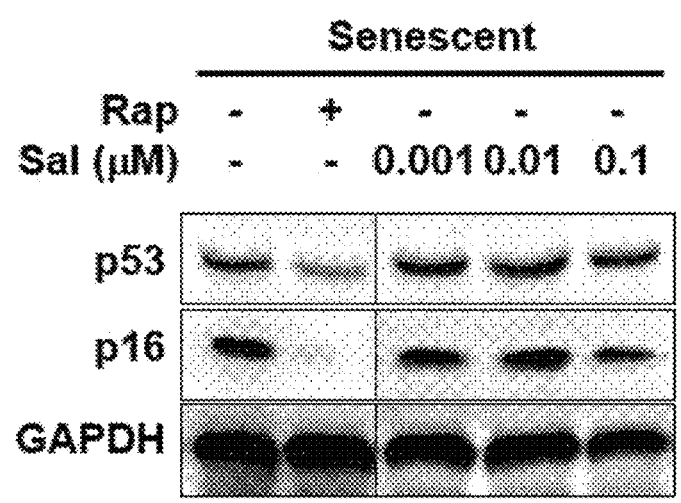
Figure 2D:
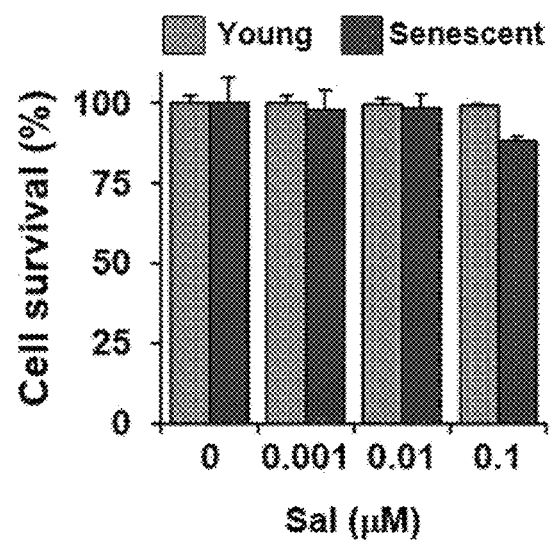

As a result of treatment with increasing the concentration of salinomycin in young fibroblasts and replicative senescent fibroblasts, SAβG activity was decreased in senescent cells in a concentration-dependent manner as shown in FIG. 2A and FIG. 2B, and as shown in FIG. 2C, it was confirmed that the expression of p53 and p16 proteins known as aging indicators was reduced. On the other hand, there was no change in cell survival in young cells and senescent cells as shown in FIG. 2A and FIG. 2D.

From the above results, it was confirmed that salinomycin acts as a senomorphics capable of changing the function and morphology of senescent cells into those of young cells in human fibroblasts.

2. Confirmation of Senomorphics Action of Salinomycin on Human Umbilical Vascular Endothelial Cells Human umbilical vascular endothelial cells were treated with doxorubicin to induce early cellular aging, and then early aged cells were treated with 0.01% DMSO, 100 nM salinomycin, 100 nM rapamycin and 100 nM ABT263, and after 4 days, SAβG activity staining was performed to confirm the degree of cellular aging, and the cell growth was confirmed by CCK-8 analysis.

Figure 3A:
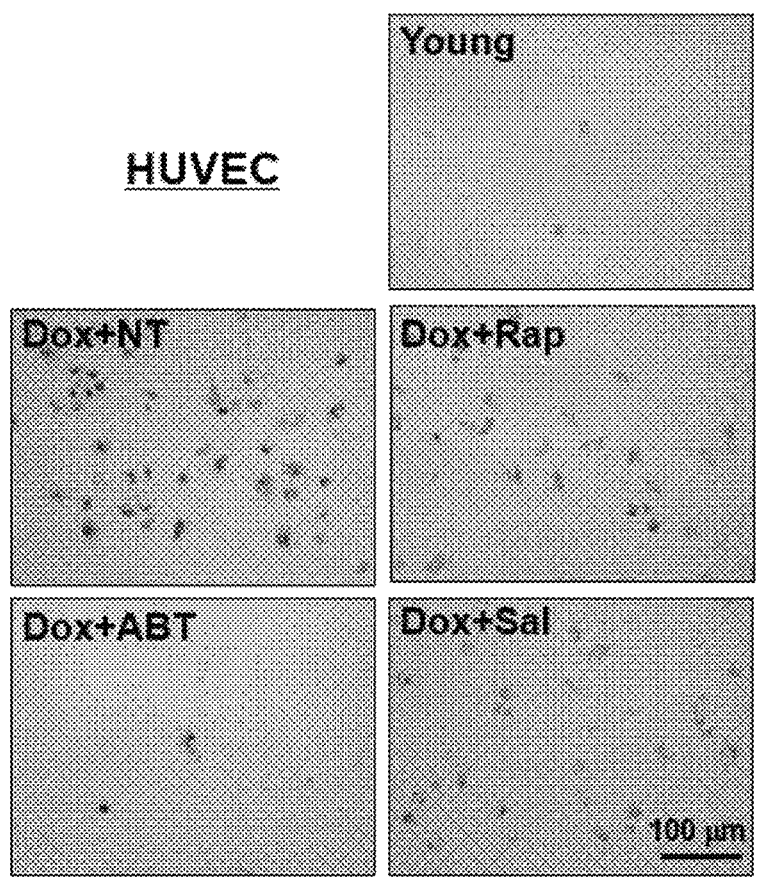
FIGS. 3A-3C show results of confirming the senomorphics action of salinomycin in premature senescent vascular endothelial cells (HUVEC) by doxorubicin.
Figure 3B:
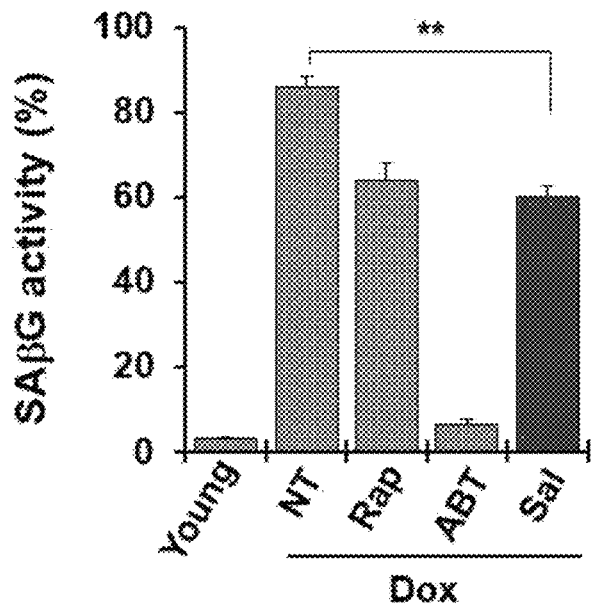
Figure 3C:
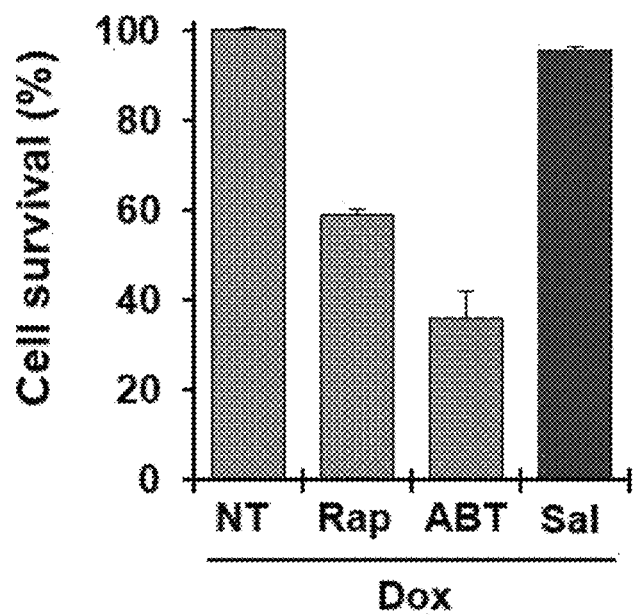

As a result, as shown in FIG. 3A and FIG. 3B, it was confirmed that the SAβG activity stating of the experimental group in which human vascular endothelial cells in which early cellular aging was induced by doxorubicin treatment was treated with 100 nM salinomycin was significantly decreased ($p<0.01$) compared to that of the DMSO-treated group. On the other hand, as shown in FIG. 3C, there was no difference in cell survival for premature senescent vascular endothelial cells compared to that for the DMSO-treated group.

From the above results, it could be confirmed that salinomycin can act as a senomorphics capable of restoring the function and morphology of aged vascular endothelial cells into those of young cells.

Figure 4A:
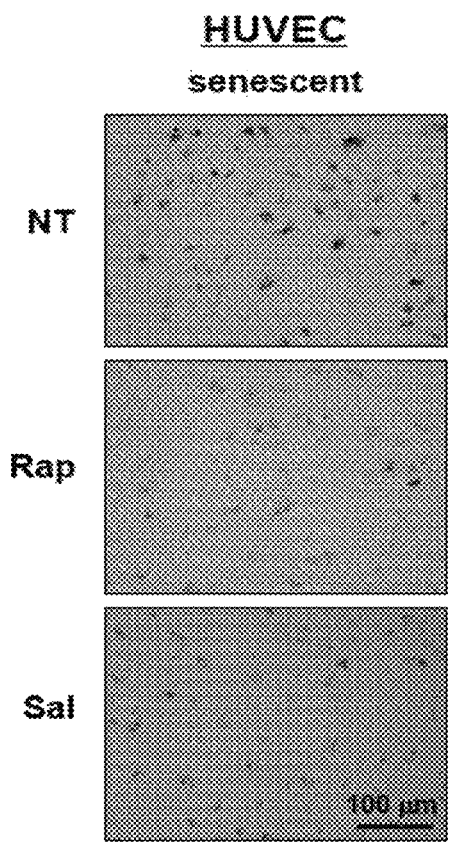
FIGS. 4A-4C show results of confirming the senomorphics action of salinomycin in replicative senescent vascular endothelial cells (HUVEC)
Figure 4B:
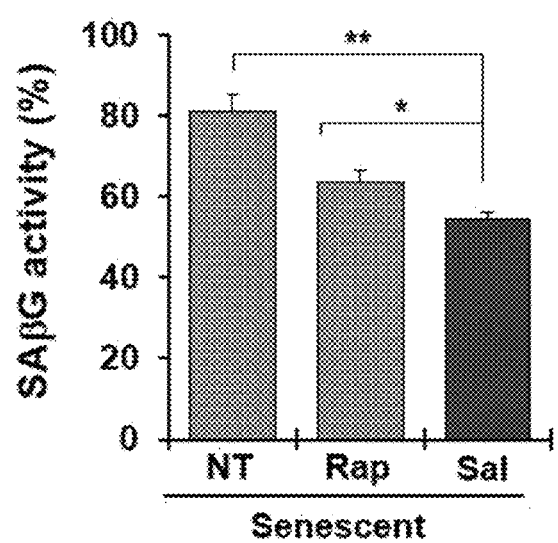
Figure 4C:
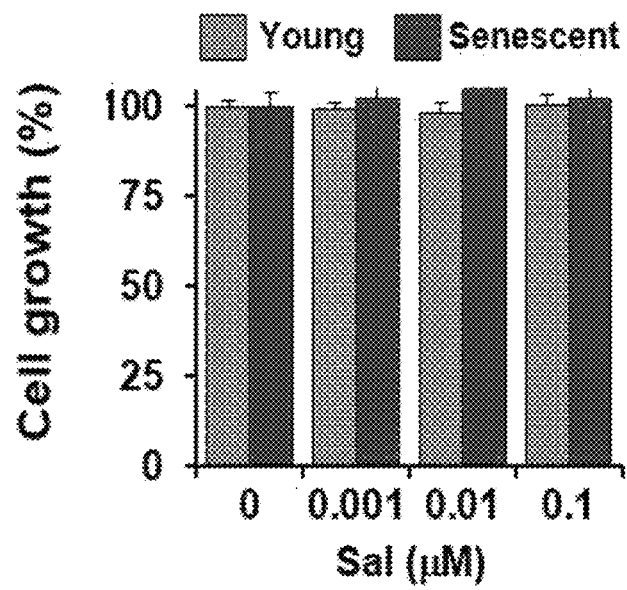

In addition, as a result of confirming whether salinomycin acts as a senomorphics for not only early senescent cells but also replicative senescent vascular endothelial cells, SAβG activity decreased in replicative senescent vascular endothelial cells by treatment with salinomycin as shown in FIG. 4A and FIG. 4B. In the CCK-8 analysis result of FIG. 4C, it was confirmed that salinomycin did not affect the cell survival of vascular endothelial cells, as in early senescent cells.

From the above results, it was confirmed that salinomycin acts as a senomorphics capable of restoring the function and morphology of senescent cells to those of young cells in human vascular endothelial cells.

<Example 2> Confirmation of Senolytics Action of Salinomycin

1. Confirmation of Senolytics Action of Salinomycin on Human Retinal Pigmented Epithelial Cells Human retinal pigmented epithelial cells were treated with doxorubicin to induce early cellular aging, and then early aged cells were treated with 0.01% DMSO, 100 nM salinomycin, and 100 nM rapamycin, and 4 days later, the cell survival was confirmed by CCK-8 analysis.

Figure 5A:
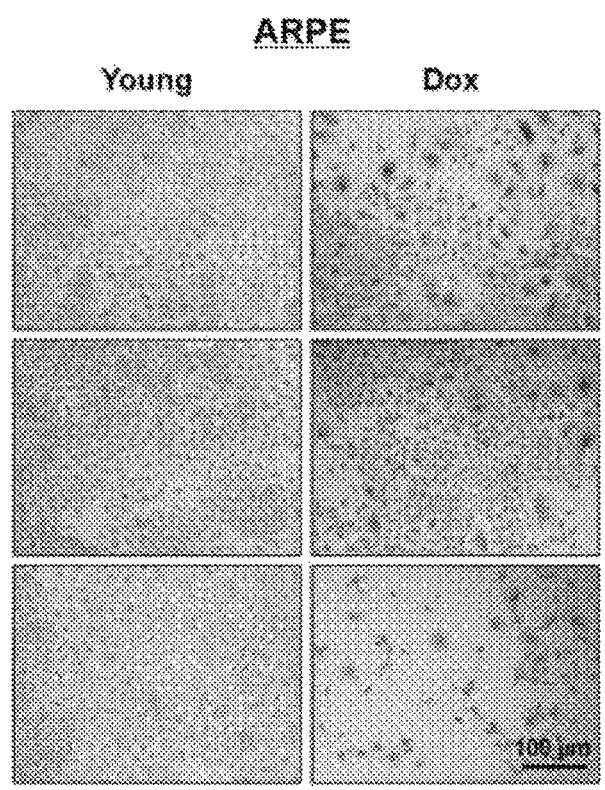
FIGS. 5A-5C show results of confirming the senomorphics action of salinomycin in premature senescent retinal pigmented epithelial cells (ARPE) by doxorubicin.
Figure 5B:
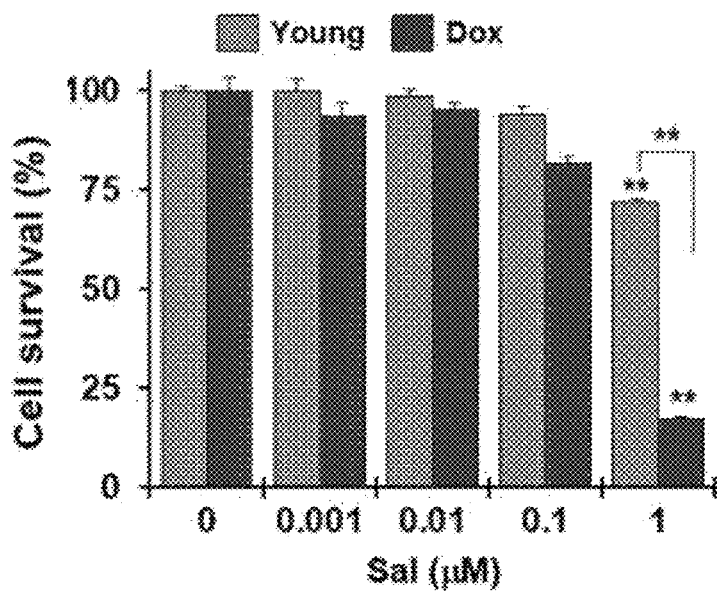

As a result, as shown in FIG. 5A and FIG. 5B, it was confirmed that in the experimental group treated with salinomycin in the human retinal pigmented epithelial cells in which early cellular aging was induced by doxorubicin treatment, cell survival was significantly ($p<0.01$) reduced compared to the DMSO-treated group.

Figure 5C:
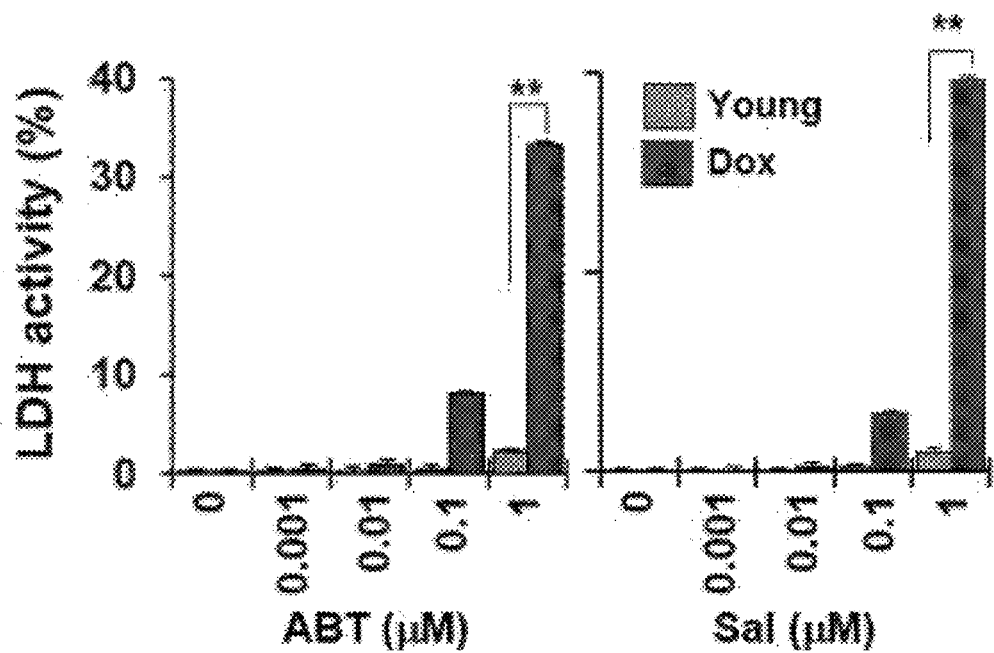

In addition, as a result of analyzing the cytotoxicity of salinomycin against senescent cells by LDH activity as shown in FIG. 5C, it was confirmed that the activity was significantly increased ($p<0.01$) in senescent cells compared to that in young cells.

From the above results, it was confirmed that salinomycin acts as a senolytics that selectively kills senescent cells in human retinal pigmented epithelial cells.

<Example 3> Confirmation of Effect of Salinomycin on Human HK2 Cells

Human HK2 cells were treated with doxorubicin to induce early cellular senescence, and then early senescent cells were treated with 0.01% DMSO, 100 nM salinomycin, 100 nM rapamycin and 100 nM ABT263, and after 4 days, SAβG activity staining was performed to confirm the degree of senescence of the cells, and cell survival was confirmed by performing CCK-8 analysis.

Figure 6A:
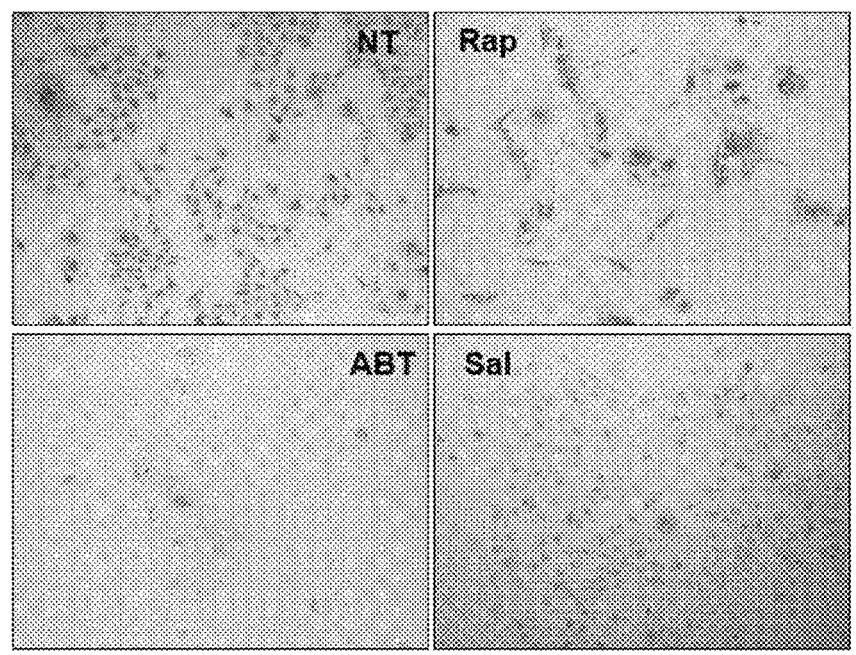
FIGS. 6A-6C show results of confirming the effect of salinomycin in premature senescent renal tubular cells (HK2) by doxorubicin.
Figure 6B:
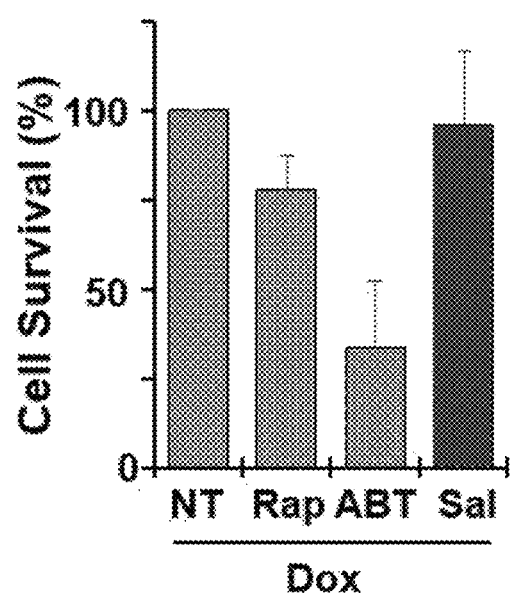
Figure 6C:
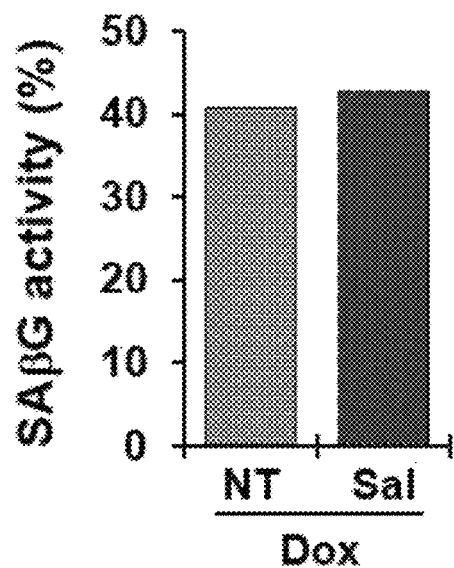

As a result, when salinomycin was treated as shown in FIG. 6A to FIG. 6C, there was no change in survival and SaβG activity of early senescent HK2 cells compared to the DMSO-treated group.

From the above results, it was confirmed that the senescent cell-specific effect of salinomycin on human HK2 cells did not appear.

<Example 4> Confirmation of Salinomycin Efficacy on Renal Fibrosis Induced by Renal Ischemia-Reperfusion Injury As renal fibrosis induced by renal ischemia-reperfusion injury has been reported to be associated with cellular aging of the tissue (Schmitt R et al., Kidney international. 2017), the left renal blood vessels of mice were ligated and released for 35 minutes to induce ischemia-reperfusion injury for confirming the effect of salinomycin on renal fibrosis.

Figure 7A:
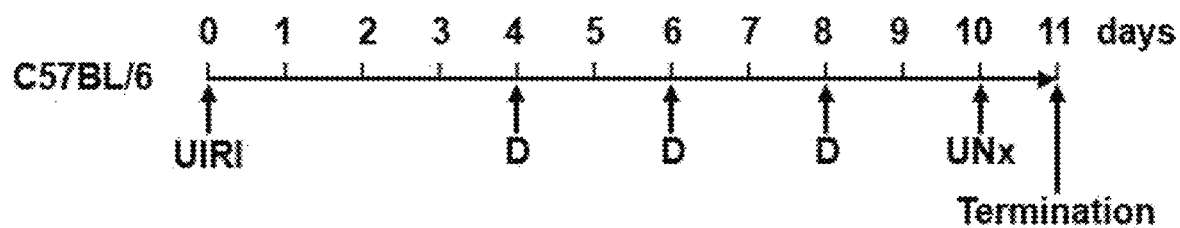
FIGS. 7A-7M show results of confirming the efficacy of salinomycin on renal fibrosis induced by renal ischemia-reperfusion injury in mice.

After 4 days, 2.5 μl of 10 mM salinomycin was diluted in 100 μl phosphate buffer solution at intervals of 2 days and injected intraperitoneally 3 times (Sal group), a group that did not induce ischemia-reperfusion injury (Sham group) and an ischemia-reperfusion injury group (PBS) were designated as a control group, and the right kidney was removed on the 10th day of the ischemia-reperfusion injury, and sacrificed on the 11th day as shown in FIG. 7A, and the body weight before the ischemia-reperfusion injury and the body weight change on the 11th day were investigated.

Figure 7B:
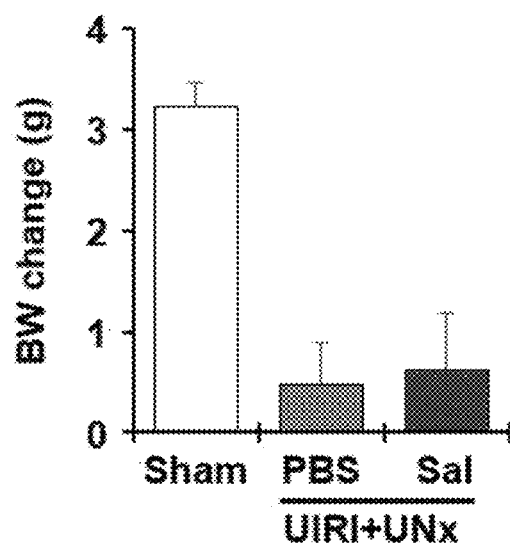
Figure 7C:
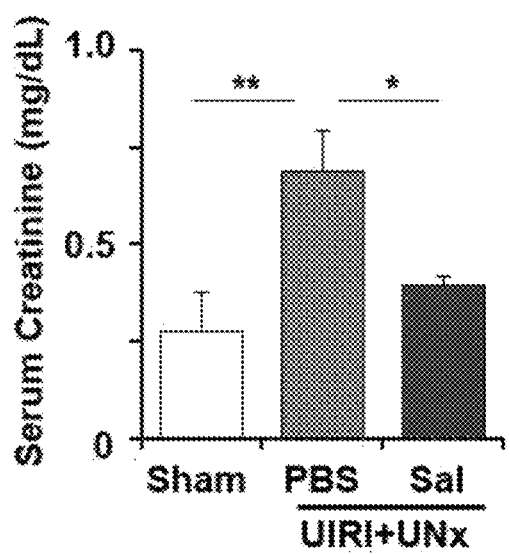
Figure 7D:
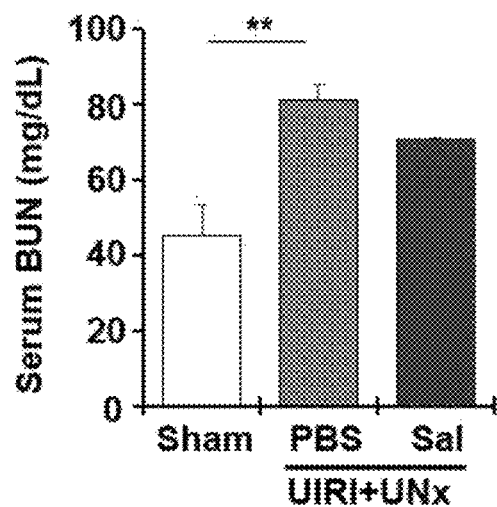

As a result, as shown in FIG. 7B, the weight gain of the PBS group or the Sal group was significantly reduced compared to the Sham group and referring to FIG. 7C and FIG. 7D, it was confirmed that plasma creatinine and BUN were decreased in the Sal group compared to the PBS group.

Figure 7E:
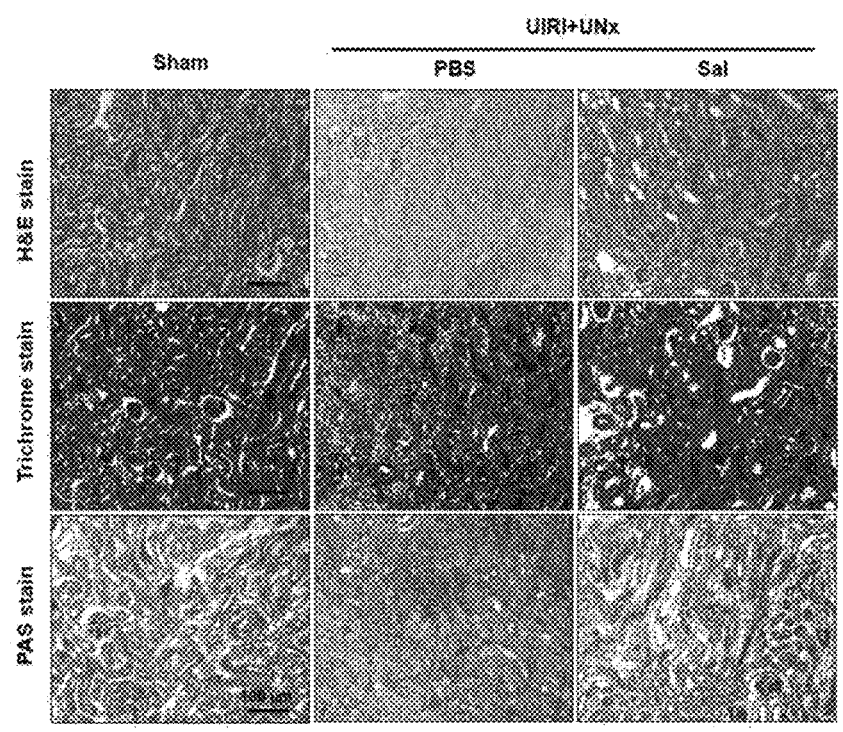
Figure 7F:
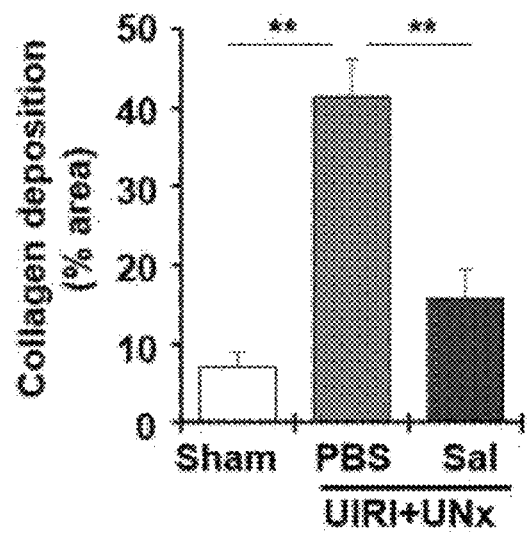

In addition, as a result of renal tissue specimen examination, as shown in FIG. 7E and FIG. 7F, damage to the renal tubules was significantly reduced in the Sal group compared to the PBS group, and the result of confirming the degree of tissue fibrosis by trichrome staining in the Sal group was also significantly reduced compared to that in the PBS group.

When cell aging occurs in tissues, lipofuscin is known to increase, and as it has been reported that cellular aging can be measured to replace SAβG staining (32), lipofuscin in tissues was stained with Sudan Black B.

Figure 7G:
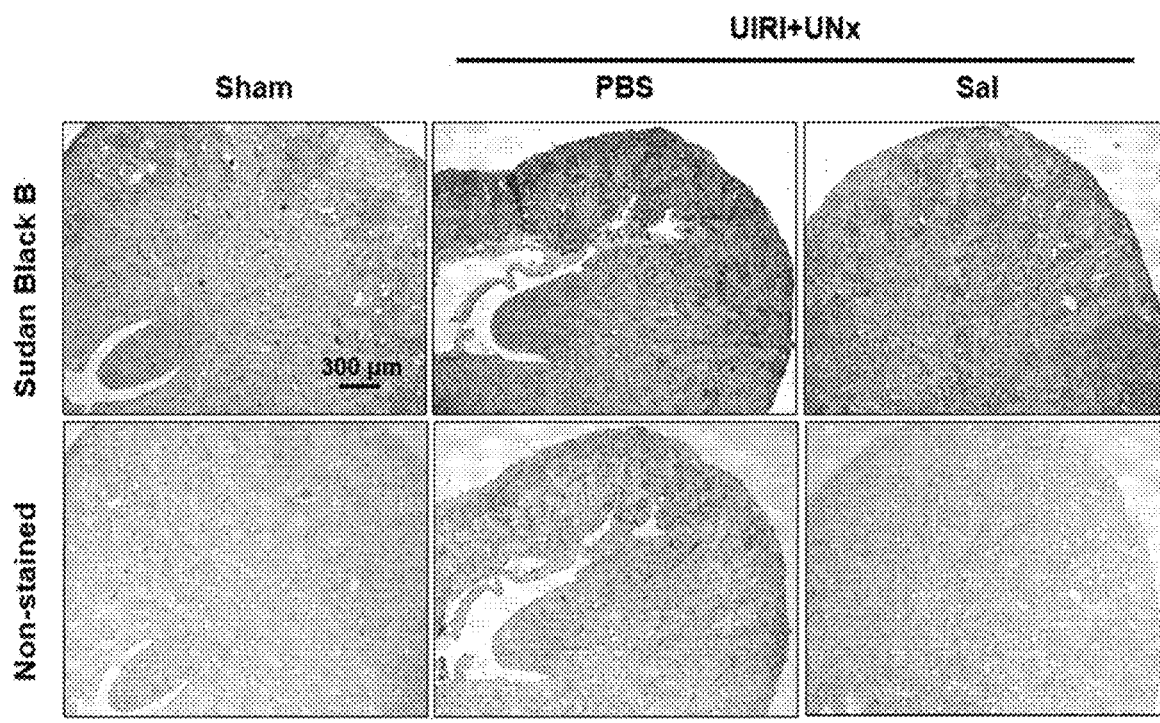
Figure 7H:
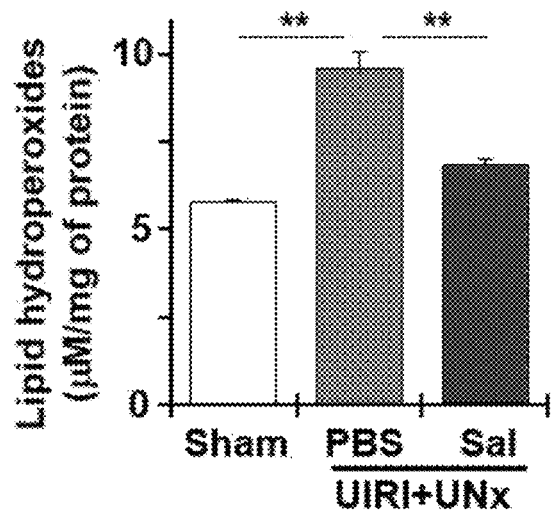
Figure 7I:
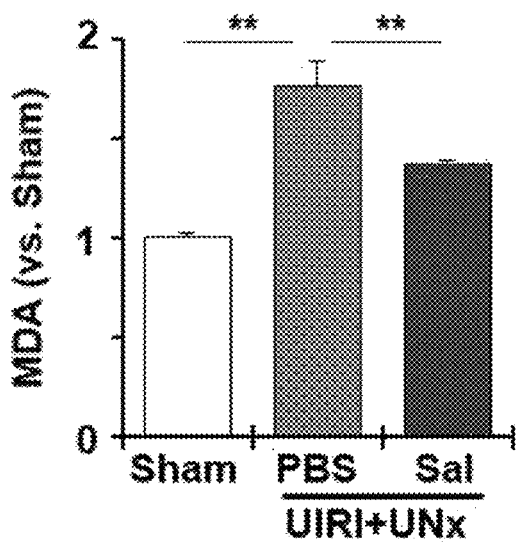
Figure 7J:
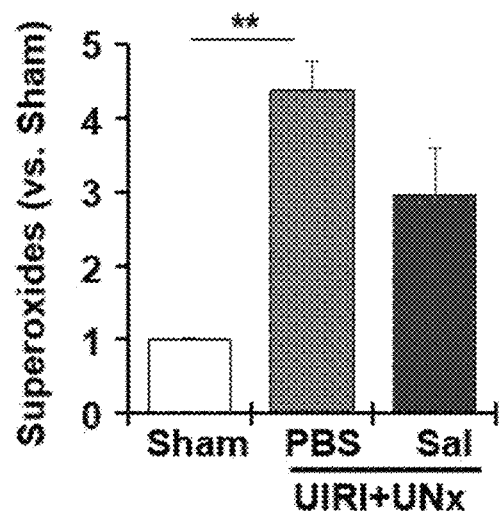

As a result, it was confirmed that the staining intensity was decreased in the Sal group compared to the PBS group, as shown in FIG. 7G. In addition, as a result of confirming the degree of oxidation of lipids with lipid peroxides and MDA by pulverizing the tissue, it was confirmed that it was significantly reduced in the Sal group compared to the PBS group as shown in FIG. 7H and FIG. 7I, and as shown in FIG. 7J, superoxides, a kind of reactive oxygen species, were also decreased in the Sal group compared to the PBS group.

Figure 7K:
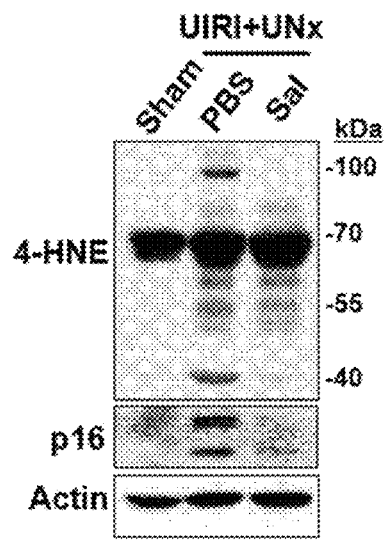
Figure 7L:
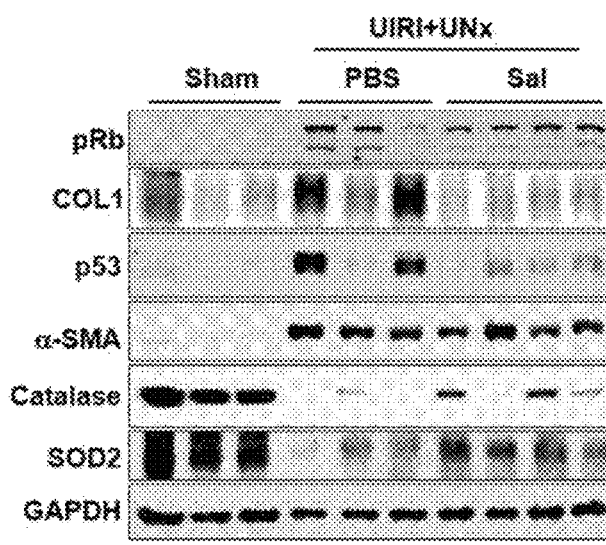
Figure 7M:
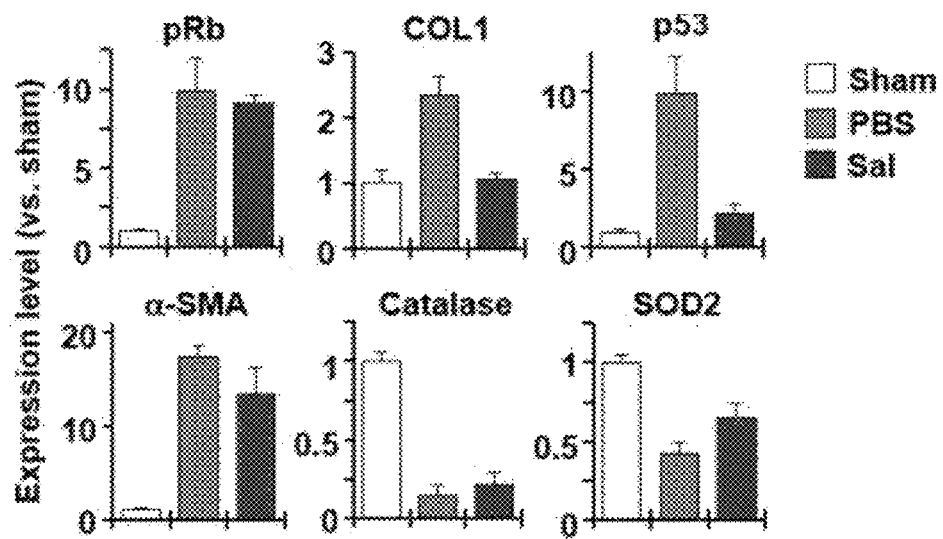

By separating the protein from the tissue, the expression levels of 4-HNE as an oxidative stress marker, and p16 as a cellular aging marker, were confirmed by Western blot, and as a result, a marked decrease in expression was observed in the Sal group compared to the PBS group as shown in FIG. 7K. In addition, as shown in FIG. 7L and FIG. 7M, it was confirmed that the expression of pRb as a cell proliferation marker, type 1 collagen (COL1) and α-SMA as fibrosis markers, and p53 as a cellular aging marker were also decreased in the Sal group compared to the PBS group. On the other hand, it was confirmed that the expression of the antioxidant enzymes catalase and SOD2 was increased in the Sal group compared to that in the PBS group.

From the above results, it was confirmed that salinomycin is effective in inhibiting renal fibrosis induced by ischemia-reperfusion injury of the kidney by changing the function of senescent cells.

Figure 8B:
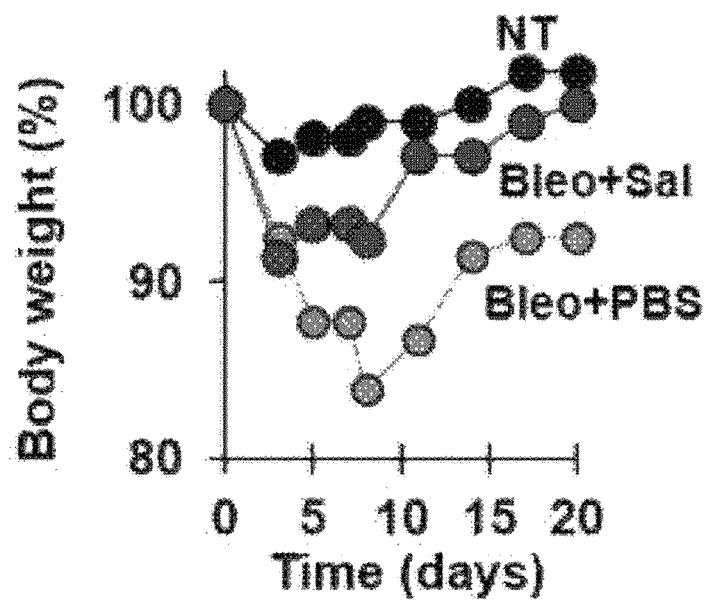

<Example 5> Confirmation of Salinomycin Efficacy on Pulmonary Fibrosis by Bleomycin As lung fibrosis induced by bleomycin in mice has been reported to be associated with cellular aging of lung tissue (Schafer M J et al., Nature communications. 2017), the efficacy of salinomycin was confirmed in experimental animals induced lung fibrosis First, as a result of investigating the body weight before the induction of lung fibrosis and the body weight change on the 20th day, as shown in FIG. 8A, the weight gain in the PBS group and the Sal group was significantly reduced compared to that in the NT group, but the weight of the Sal group was further increased compared to the PBS group as shown in FIG. 8B.

In addition, lung tissue samples were prepared, and hematoxylin-eosin staining and trichrome staining were performed to confirm the degree of damage to the lung tissue and the degree of lung fibrosis.

Figure 8C:
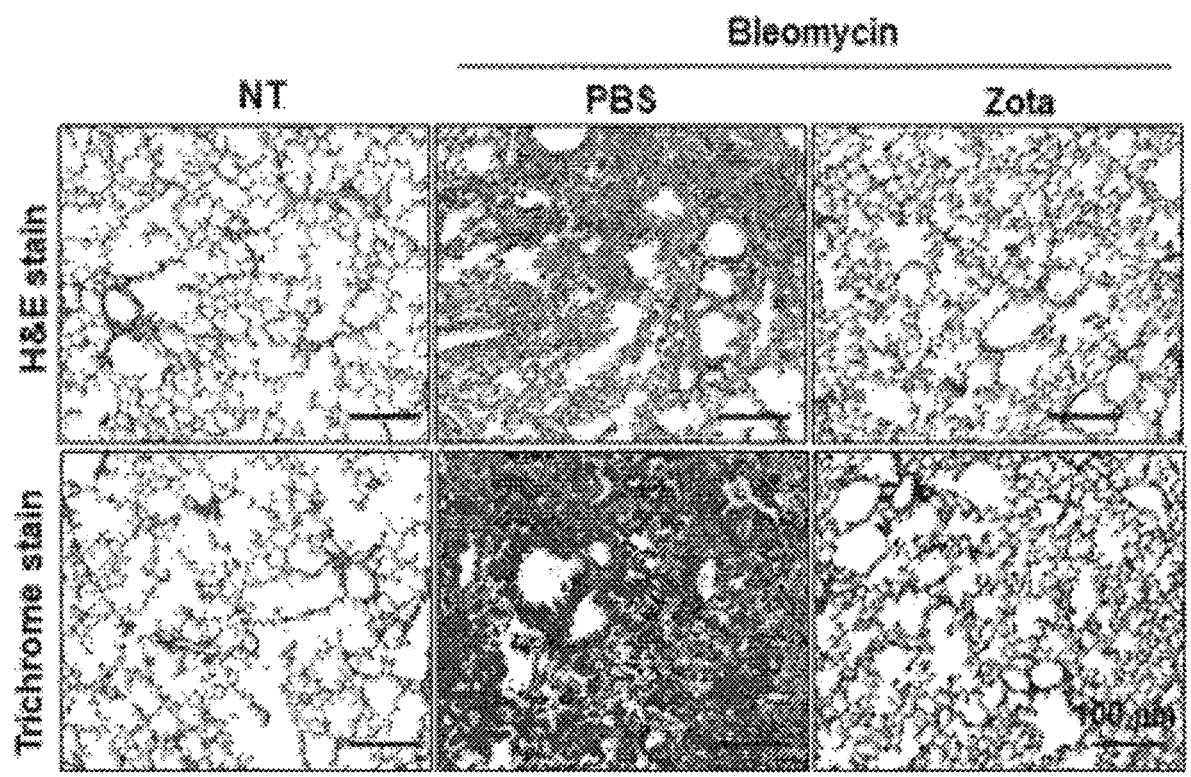
Figure 8D:
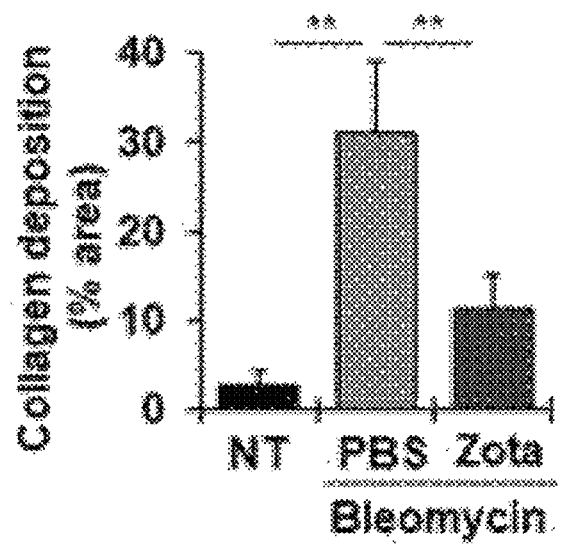

As a result, as shown in FIG. 8C and FIG. 8D, it was confirmed that the degree of lung tissue damage and lung fibrosis in the Sal group were statistically significantly reduced compared to those in the PBS group.

From the above results, it was confirmed that salinomycin exhibits an effect of inhibiting pulmonary fibrosis induced by bleomycin.

<Example 6> Confirmation of Efficacy of Salinomycin on Peritoneal Fibrosis Induced by Chlorhexidine Gluconate (CHG)

Peritoneal fibrosis is a side effect that occurs frequently in patients who have undergone peritoneal dialysis, and may cause a problem of reducing peritoneal dialysis efficiency.

Long-term peritoneal dialysis increases reactive oxygen species by components of peritoneal dialysis fluid, and induces peritoneal fibrosis due to chronic inflammation. In this process, epithelial to mesenchymal transition of peritoneal mesenchymal cells by TGF-β1 is known to play an important role, and TGF-β1 is well known to induce cellular aging.

In order to confirm the effect of salinomycin on the peritoneal fibrosis, a 0.1% CHG solution was injected intraperitoneally for 20 days at intervals of 2 days, and salinomycin or DMSO-phosphate buffer solution was injected intraperitoneally from the 9th day.

Abdominal wall tissue specimens were prepared, and hematoxylin-eosin staining and trichrome staining were performed, and then the thickness of the peritoneal mesothelial cell layer and the degree of peritoneal fibrosis were confirmed.

Figure 9C:
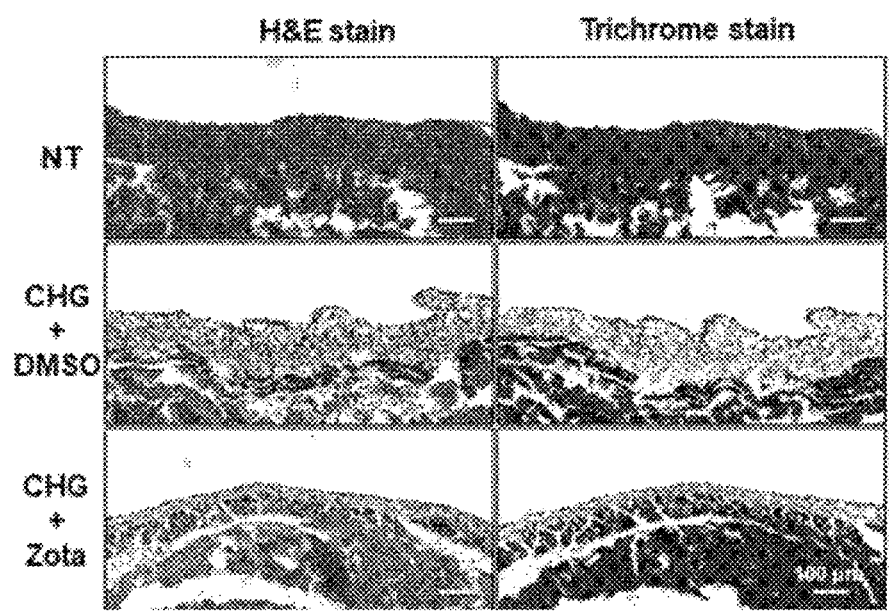
Figure 9D:
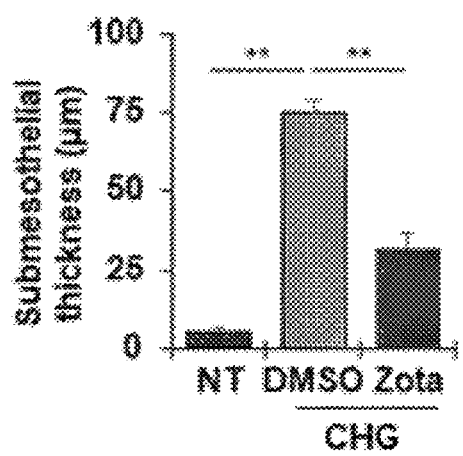

As a result, it was confirmed that the thickness of the peritoneal mesothelial cell layer in the salinomycin-treated group (Sal group) was significantly reduced compared to that in the DMSO-phosphate buffer solution (DMSO group) as shown in FIG. 9C and FIG. 9D, and the degree of fibrosis was also decreased.

From the above results, it was confirmed that salinomycin inhibits peritoneal fibrosis induced by CHG.0

While the present invention has been particularly described with reference to specific examples thereof, it is apparent that this specific description is only a preferred example and that the scope of the present invention is not limited thereby to those skilled in the art. Accordingly, the practical scope of the present invention is defined by the appended claims and their equivalents.

The invention claimed is:

1. A method for restoring function of a senescent cell to a normal cell comprising administering a pharmaceutical composition comprising salinomycin as an active ingredient to a subject in need of restoring function of the senescent cell to the normal cell,
   wherein the senescent cell is selected from the group consisting of a fibroblast and a vascular endothelial cell, and
   wherein a senescence is induced by drug treatment or subculture in the senescent cell.

2. A method for killing a senescent cell comprising administering a pharmaceutical composition comprising salinomycin as an active ingredient to a subject in need of killing the senescent cell,
   wherein the senescent cell is a retinal pigmented epithelial cell, and
   wherein a senescence is induced by drug treatment or subculture in the retinal pigmented epithelial cell.

3. A method for treating a tissue fibrosis comprising administering a pharmaceutical composition comprising salinomycin as an active ingredient to a subject in need of treating tissue fibrosis.

4. The method of claim 3, wherein the salinomycin selectively kills a senescent cell or restores function or shape of the senescent cell to a normal cell to treat the tissue fibrosis.

5. The method of claim 3, wherein the tissue fibrosis is selected from the group consisting of a renal fibrosis, a pulmonary fibrosis, and a peritoneal fibrosis.

6. A method for improving aging comprising administering a pharmaceutical composition comprising salinomycin as an active ingredient to a subject in need of the improving aging.

* * * * *